United States Patent [19]

Buysch et al.

[11] Patent Number: 5,391,802

[45] Date of Patent: * Feb. 21, 1995

[54] PROCESS FOR CLEAVING POLYCARBONATES INTO BISPHENOLS AND DIARYL CARBONATES

[75] Inventors: Hans-Josef Buysch; Norbert Schön; Steffen Kühling, all of Krefeld, Germany

[73] Assignee: Bayer Aktiengesellschaft, Leverkusen, Germany

[*] Notice: The portion of the term of this patent subsequent to Nov. 30, 2010 has been disclaimed.

[21] Appl. No.: 76,715

[22] Filed: Jun. 14, 1993

[30] Foreign Application Priority Data

Jun. 22, 1992 [DE] Germany ............... 4220412

[51] Int. Cl.⁶ .............................. C07C 69/96
[52] U.S. Cl. .................... 558/265; 558/266; 558/267; 558/268; 558/269; 558/277
[58] Field of Search ............... 558/265, 266, 267, 268, 558/269, 277

[56] References Cited

U.S. PATENT DOCUMENTS 5,266,716 11/1993 Buysch et al. .............. 558/260

FOREIGN PATENT DOCUMENTS 45600 11/1963 Germany .

Primary Examiner—José G. Dees
Assistant Examiner—Dwayne C. Jones
Attorney, Agent, or Firm—Joseph C. Gil; Aron Preis

[57] ABSTRACT

A process is disclosed for cleaving polycarbonates into bisphenols and diaryl carbonates by transesterifying with phenols in the presence of catalysts. The process entails isolating bisphenols from the product of the transesterification, and subjecting the remaining mixture which contains phenols and diaryl carbonates to flash distillation. The phenols and diaryl carbonates are distilled off and separated, and the diaryl carbonates are recovered.

6 Claims, No Drawings

5,391,802

PROCESS FOR CLEAVING POLYCARBONATES INTO BISPHENOLS AND DIARYL CARBONATES

FIELD OF THE INVENTION

The invention relates to polycarbonates and especially to a catalytic process reacting polycarbonates with phenols to produce bisphenols and diaryl carbonates.

1. Summary of the Invention

This invention provides a process for cleaving polycarbonates into bisphenols and diaryl carbonates by trans-esterifying with phenols in the presence of catalysts. The process is characterized in that the bisphenols are isolated from the product of the transesterification, the remaining mixture is subjected to a flash distillation, phenols and diaryl carbonates are distilled off and separated, and the diaryl carbonates are recovered.

2. Background of the Invention

It is known to cleave polycarbonates with phenols. Thus in DDR-PS 45,600 a process is described according to which bisphenol A polycarbonates are reacted with phenol in the presence of basic catalysts, the mixture treated with dilute caustic soda solution, wherein diphenyl carbonate precipitates as an insoluble compound, and the phenolic compounds are precipitated with acids from the caustic soda solution and finally separated into phenol and bisphenol A. This is a very expensive and involved process that requires enormous amounts of caustic soda solution and acids (1 mole of each per mole phenolic OH) water and solvents. It also requires enormous reaction volumes, and therefore large apparata, and produces disproportionately large quantities of salt- and phenolcontaining waste water. Technical exploitation of this process is therefore not possible. A reworking of the process has proved that a separation of the reaction products is not thus possible and for example the diphenyl carbonate fraction remains strongly basic and still contains oligocarbonate residues.

It has now been discovered that the aforesaid disadvantages can be avoided if from the reaction product of a polycarbonate with a phenol the bisphenol is first separated, and phenol and diaryl carbonate then distilled off from the residual mixture by means of flash distillation and recovered by fractionation.

This is a surprisingly simple and effective process for decomposing polycarbonates into monomers in high yields by transesterification, separating and purifying the latter and converting them again into high-molecular plastics.

Polycarbonates within the meaning of the invention are in general those based on aromatic dihydroxy compounds that are and can be used in technology.

Aromatic dihydroxy compounds are for example dihydroxybenzenes, dihydroxybiphenyl, dihydroxydiphenyl ether, dihydroxydiphenyl sulphide, dihydroxydiphenyl sulphone, dihydroxydiphenylmethane (bisphenol F), dihydroxydiphenylethane, dihydroxydiphenylpropane (bisphenol A), dihydroxydiphenylcyclohexane (bisphenol Z), 3,3,5-trimethyl-1,1-(dihydroxydiphenyl)cyclohexane, α,α'-(dihydroxyphenyl)diisopropylbenzenes, dihydroxybenzophenone or mixtures of these aromatic dihydroxy compounds, preferably bisphenol A, bisphenol z, dihydroxydiphenylmethane and 3,3,5-trimethyl-1,1-(dihydroxydiphenyl)cyclohexane: bisphenol A is particularly preferred.

The polycarbonates to be cleaved according to the invention are known from the literature (see for example the monograph "H. Schnell, Chemistry and Physics of Polycarbonates, Interscience Publishers, New York, 1964").

The polycarbonates to be cleaved can have molecular weights Mw (weight-average, determined for example by gel permeation chromatography) of 5,000 to 200,000, preferably 10,000 to 80,000. The molecular weights can also be determined in a known way by determining the relative viscosity in $CH_2Cl_2$ at 25° C. and a concentration of 0.5 wt. %. Preferred polycarbonates to be cleaved are the aromatic, thermoplastic polycarbonates that preferably are produced from at least one of the diphenols listed below. These are 4,4'-dihydroxy-diphenyl, 2,2-bis(4-hydroxyphenyl)propane (bisphenol A), 2,4-bis-(4-hydroxyphenyl)-2-methylbutane, 1,1-bis-(4-hydroxyphenyl)cyclohexane, α,α'-bis(4-hydroxyphenyl)-p-diisopropylbenzene, 2,2-bis-(3-chloro-4-hydroxyphenyl) propane, 2,2-bis-(3,5-dichloro-4-hydroxyphenyl) propane, 2,2-bis-(3,5-dibromo-4-hydroxyphenyl)-propane and 1,1-bis(4-hydroxyphenyl)-3,3,5-trimethylcyclohexane.

The polycarbonates to be cleaved according to the invention can also be branched in the usual way by the incorporation of three or more as trifunctional compounds. These are optionally isolated together with the bisphenols and optionally separated.

The bisphenols are removed from the cleavage mixture obtained from the transesterification essentially by crystallization. This can be done by bringing about the crystallization of the bisphenols by cooling, which can then be undertaken with the aid of filters, nutsches, sedimenters, decanters, centrifuges and other apparata known to the expert for such purposes.

The bisphenols can also be caused to crystallize out from the cleavage mixture by suitable solvents or their mixtures.

Suitable solvents are aliphatic and aromatic hydrocarbons and their halogen compounds. The following may be mentioned as examples: hexane, heptane, isooctane, isononane, benzene, toluene, o-, m- and p-xylene, cumene, cymene, diisopropylbenzene, tert-butylbenzene, tertbutyltoluene, cyclohexane, methylcyclopentane, methylcyclohexane, dimethylcyclohexane, methylene chloride, chloroform, chlorobenzene, chlorotoluene, dichlorobenzene, chlorocumene and chloroxylene. These solvents can also optionally be added to the transesterification mixture from the start onwards.

The bisphenols can naturally be purified by further steps such as recrystallization or absorptive removal of interfering and colouring impurities.

The monophenolic chain terminators released from the polycarbonates in the process of the invention are recovered by distillation as the corresponding carbonates.

Suitable phenols for the process according to the reaction are in particular low-boiling phenols such as phenol itself, cresols, chlorophenols, xylenols, isopropylphenols and p-tert-butylphenol, preferably phenol and cresols, particularly preferably phenol.

The molar ratio of polycarbonate (as molecular weight unit) to phenol is between 1:1 to 1:20, preferably 1:1.5 to 1:18, particularly preferably 1:2 to 1:12.

The use of phenol also has the following advantage:

If for example phenol is used in the cleavage of bisphenol A polycarbonate, at first a rapid pre-decomposition of the polycarbonate is initiated when the polycarbonate is dissolved in phenol in the presence of the catalyst. As a result, highly concentrated solutions of partly degraded polycarbonate with low viscosity can be produced, from which additives and fillers can easily be removed by filtration, centrifuging or sedimentation, and colouring impurities and dyestuffs by adsorptive processes.

Moreover, the bisphenol A can be obtained crystalline in the form of its known 1:1 adduct with phenol, which can be freed from phenol by known methods, such as by treatment with sol vents or by thermal desorption. That also permits, for example, the coupling of this process with any optionally available bisphenol-A manufacture, which can take on further purification and working-up of the bisphenol A adduct in known manner to bisphenol A.

Possible catalysts for the polycarbonate cleavage according to the invention are known in the literature. (See for example DDR Patents 45,600 and 46,363, DE-AS 1,155.,452 and JA 61/27 203A). Suitable catalysts are for example hydrides, oxides, hydroxides, alcohols, amides or salts of alkali metals such as lithium, sodium, potassium, rubidium and caesium, preferably of lithium, sodium and potassium, particularly preferably of sodium and potassium. Salts of alkali metals are those of organic and inorganic acids, such as for example of acetic acid, propionic acid, butyric acid, benzoic acid, stearic acid, carbonic acid, hydrochloric acid, HBr, HI, nitric acid, $H_2SO_4$, HF, phosphoric acid, boric acid, tin acids and antimony acids.

Preferred alkali metal catalysts are alkali metal oxides, hydroxides, alcoholates, acetates, propionates, benzoates, carbonates and hydrogen carbonates; particularly preferred alkali metal catalysts are the alkali metal hydroxides, alcoholates, acetates, benzoates and carbonates.

The alkali metal catalysts are used in amounts of 0.0001 to 20 mole % in particular of 0.001 to 10 mole % and particularly preferably in amounts of 0.005 to 5 mole % relative to one mole carbonate unit in the polycarbonate to be cleaved.

The alkali metal catalysts can optionally be used in combination with complexing substances, such as for example crown ethers, polyethylene glycols or bicyclic nitrogen-containing cryptands.

A suitable crown ether for example is dibenzo-18-crown-6, a nitrogen-containing cryptand for example is 1,9-dimethyl-1, 9-diaza-dibenzo-18-crown-6.

The complexing substances are used in amounts of 0.1 to 200 mole preferably of 1 to 100 mole relative to 1 mole alkali metal compound.

Nitrogen-containing bases are also catalysts for the polycarbonate cleavage according to the invention, as for example secondary and tertiary amines such as triethylamine, tributylamine, methyldibenzylamine and dimethylcyclohexylamine, diazabicycloundecane or diazabicyclononane.

The nitrogen-containing bases are used in amounts of 0.001 to 20 mole %, preferably of 0.005 to 10 mole %, particularly preferably 0.01 to 3 mole %, relative to 1 mole carbonate unit in the polycarbonate to be cleaved.

Complexes or salts or compounds of magnesium, calcium, barium, zinc, tin, titanium or zirconium are also catalysts for the polycarbonate cleavage according to the invention. Examples of such systems are tin methoxide, dimethyltin, dibutyltin oxide, dibutyltin dilaurate, tributyltin hydride, tributyltin chloride, tin (II) ethylhexanoate, zirconium alkoxides (methyl, ethyl, butyl), zirconium(IV) halides (F, Cl, Br, I), zirconium nitrates, zirconium acetylacetonate, titanium alkoxides (methyl, ethyl, isopropyl) titanium acetate and titanium acetylacetonate.

These catalysts are used in amounts of 0.0001 to 20 mole %, preferably of 0,001 to 10 mole % and particularly of 0.005 to 5 mole %, relative to 1 mole carbonate unit in the polycarbonate to be cleaved.

The catalysts to be used are charged to the corresponding phenol either in bulk or as a solution of the polycarbonate melt. If an alkali metal catalyst is used in this connection, preferably alkali alcoholates or alkali phenolates can be used. The catalysts to be used for the polycarbonate cleavage can also be charged dissolved in phenols in the phenol of the polycarbonate melt or of the polycarbonate solution provided for the polycarbonate cleavage.

After the transesterification, the catalysts can remain in the cleavage product during the further working up. They can also be deactivated by additions, e.g. of strong acids in the case of alkali compounds, or by other measures, such as adsorption.

The temperatures for the cleavage of the polycarbonates with the phenols can be between about 100° C. and 320° C., preferably between 130° C. and 290° C., particularly preferably between 150° C. and 280° C. in the case of temperatures above the boiling point of the phenol, the operation must be carried out under appropriate pressure in order to maintain the phenols in the liquid phase.

A flash distillation for the recovery of the diaryl carbonates within the meaning of the invention is a rapid separation of the more volatile from the less volatile compounds that can best be carried out from rapidly heated films and liquids. For example falling-film evaporators, thin-film evaporators, helical-tube evaporators, and circulating- or climbing-film evaporators are suitable for that.

This operation suitably proceeds at reduced pressure of 0.01 to 800 mbar, preferably 0.1 to 500 mbar, particularly preferably 0.5 to 200 mbar.

The temperatures are so chosen that at a given pressure the phenols and diaryl carbonates distill off rapidly, as can optionally be determined easily by appropriate preliminary experiments.

The whole process can be carried out discontinuously, semicontinuously or continuously.

A batchwise process requires no particular explanation.

A semicontinuous procedure can be carried out for example by feeding a continuous distillation unit from a mother liquor vessel that receives mother liquor in turn from two separate melting, cleavage and crystallization plants operated alternately. The crystallization can also, however, be arranged continuously in a known way, and connected to separately and alternately operated melting and cleavage apparatuses. Finally the cleavage can also be carried out continuously for example in a sufficiently long tubular reactor, that again is fed from two melting vessels operated alternately.

A fully continuous operating procedure can be realized for example by continuously feeding polycarbonate, phenol and catalyst into a screw reactor or other suitable mixing unit, producing melt or solution and transesterification products, that optionally are then cooled in countercurrent with fresh educt and are introduced into a continuous crystallization unit, from which bisphenols and mother liquor can be drawn, which latter can then be separated in a continuous distillation into phenols and diaryl carbonates. The bottom fraction from the distillation is led back again, after the purging of possible by-products into the screw reactor.

In this way in a simple, fully continuous process, polycarbonates can be decomposed in excellent yields into their monomers which, if desired, can immediately be built up again by condensation to high-molecular plastics.

The process according to the invention for the cleavage of polycarbonates is usable generally for a great variety of polycarbonate moulding materials. However, it does not primarily serve the purpose of synthesizing in this way diphenols and carbonate esters, but above all of chemically cleaving polycarbonate moulding materials no longer otherwise usable, thus for example wastes arising during the production of moulded bodies, cuttings arising or moulded parts that have become unusable, polycarbonate refuse etc., into monomeric components, which can be purified simply and therefore are usable for the fresh production of polycarbonates or for other purposes: the dihydroxy compounds for example for the production of epoxy resins and the carbonate esters as solvents or for syntheses in organic chemistry.

Accordingly the polycarbonates to be cleaved according to the invention can also contain the usual additives, such as mineral fillers like quartz powder, glass powder, glass fibers, stabilizers, UV protective agents, lubricants, pigments and dyestuffs, as well as polymeric blending components such as for example vinyl polymers from styrene, acrylonitrile and butadiene.

The additives insoluble in phenols in the polycarbonate melt or in the polycarbonate solution are removed by filtration, centrifugation or sedimentation before feeding to the transesterification; the additives soluble in the polycarbonate melt or in the polycarbonate solution can be removed from the diphenols obtained by distillation or crystallization or adsorption.

Colouring impurities that are introduced by the polycarbonate used can, apart from distillation or crystallization, also be removed by adsorptive purification processes, for example on activated carbon, kieselguhr, cellulose or zeolites. These adsorptive purification processes can be carried out both with the polycarbonate solution in phenols and with the solutions arising of the dihydroxy compounds.

The polycarbonate cleavage process according to the invention is therefore very suitable for the recycling of polycarbonate wastes.

The invention is further illustrated but is not intended to be limited by the following examples in which all parts and percentages are by weight unless otherwise specified.

EXAMPLES

Example 1

254 g (corresponding to 1 molecular weight unit) of bisphenol A polycarbonate with a molecular weight of about 28,000 and 470 g (5 moles) phenol were melted under nitrogen and heated at 170° to 180° C. To that, 0.5 g potassium hydroxide, dissolved in a little phenol, was added dropwise in 10 min., the mixture stirred for about 1 h at 170° C., and 0.25 g phosphoric acid added. After cooling to 40° to 42° C., 372 g crystals precipitated, essentially of the 1:1 adduct of phenol and bisphenol A, that were removed by suction-aided filtration, 350 g of a clear mother liquor being separated off. The adduct (372 g) was recrystallized from 400 g phenol, 233 g of purified crystalline adduct and 530 g mother liquor being obtained.

The united mother liquors were distilled at 180° C. jacket temperature and 1 to 2 mbar by means of a thin-film evaporator. In the course of this, 765 g of a distillate and 117 g of a viscous bottom fraction, solid when cold and consisting essentially of oligocarbonate, were obtained. The distillate was separated by fractional distillation into 660 g phenol and 101 g diphenyl carbonate with a melting point of 85° to 86° C.

According to the recovered fraction of 117 g, the polycarbonate used had been about 54% cleaved, and the product split into 115 g bisphenol A, contained in 233 g purified adduct, that is 50%, and 101 g diphenyl carbonate, that is 47%, relative in each case to the polycarbonate used. The yield of bisphenol A was therefore 93% of diphenyl carbonate, that is 87% of theoretical.

The distillation bottom fraction of 117 g oligocarbonate can be used in a further cleavage charge.

Example 2

Example 1 was repeated without addition of phosphoric acid. For the crystallization of the product mixture, 700 ml of a mixture of 2 parts toluene: 3 parts cyclohexane was added, the mixture stirred at room temperature and 129 g of a crystallizate still containing phenol (with 113 g bisphenol A) separated. After distilling off the solvent, the clear mother liquor of 593 g was added dropwise to a flask fitted with a high-speed stirrer that dipped into an oil bath heated at 240° C. At 1 to 2 mbar and 190° C. bottom temperature, the whole distillate came over in 60 to 70 min. It was introduced as vapor approximately in the middle of a column maintained at a temperature of 100° C., and split into 76 g diphenyl carbonate, that ran into the bottom of the column, and 512 g phenol, that passed over as top product.

There remained in the distillation flask 150 g oligocarbonate bottom product that appeared in increased amount, compared with Example 1, owing to a longer residence time in the flask and therefore more favorable condensation with diphenyl carbonate.

Therefore, relative to the polycarbonate used, 50% of bisphenol A, 33% of diphenyl carbonate and 150 g oligocarbonate were recovered.

The latter, after a further cleavage step corresponding to the above, yielded 89 g bisphenol A and 66 g diphenyl carbonate. The remaining residue of oligocarbonate can be reacted further with phenol and cleaved.

Example 3

To a melt of 470 g phenol and 254 g bisphenol A polycarbonate of molecular weight 25,000, 1.0 g potassium hydroxide is added in portions and the mixture kept for about 30 min at 170° to 180° C. To 504 g of this mixture after cooling, 750 g of a mixture of 2 parts toluene and 3 parts cyclohexane are added. By crystallization, 116 g bisphenol A with a melting point of 156° to 158° C. are obtained. The mother liquor, after removing the solvent, is subjected to a flash distillation as in Example 1.93 g diphenyl carbonate is obtained, with 95 g oligocarbonate as bottom product.

The yield of bisphenol is accordingly 72% of that theoretically possible from the 504 g of the above melt and that of diphenyl carbonate correspondingly 62 of the possible. As a result of further transesterification of the oligocarbonate with phenol, additional amounts of bisphenol A and diphenyl carbonate can be obtained, so that the total yield exceeds 90%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for cleaving polycarbonates into bisphenols and diaryl carbonates comprising
    (i) reacting a polycarbonate resin with phenol in presence of a catalyst to obtain a-product of transesterification containing bisphenol and a mixture containing phenols and diarylcarbonates,
    (ii) isolating by crystallization said bisphenol from said product of transesterification,
    (iii) subjecting said mixture to flash distillation to separate said phenol from said diaryl carbonate, and
    (iv) recovering said diaryl carbonate.

2. The process of claim 1 wherein said polycarbonate resin has a weight average molecular weight of 10,000 to 80,000.

3. The process of claim 1 wherein said polycarbonate is based on at least one dihydroxy compound selected from the group consisting of dihydroxybenzenes, dihydroxybiphenyl, dihydroxydiphenyl ether, dihydroxydiphenyl sulphide, dihydroxydiphenyl sulphone, dihydroxydiphenylmethane, dihydroxydiphenylethane, dihydroxydiphenylpropane, dihydroxydiphenylcyclohexane, 3,3,5-trimethyl-1,1-(dihydroxydiphenyl)cyclohexane, $\alpha,\alpha'$-(dihydroxyphenyl)-diisopropylbenzenes and dihydroxybenzophenone.

4. The process of claim 1 wherein said phenol is selected from the group consisting of phenol, cresol, chlorophenol, xylenol, isopropylphenol and p-tert-butylphenol.

5. The process of claim 1 wherein polycarbonate and phenol are reacted in a molar ratio therebetween of 1:1 to 1:20.

6. The process of claim 1 wherein polycarbonate and phenol are reacted in a molar ratio therebetween of 1:1.5 to 1:18.

* * * * *